United States Patent
Chen et al.

(10) Patent No.: US 11,694,374 B2
(45) Date of Patent: Jul. 4, 2023

(54) METHOD FOR GATING IN TOMOGRAPHIC IMAGING SYSTEM

(71) Applicant: Delta Electronics, Inc., Taoyuan (TW)

(72) Inventors: Sih-Yu Chen, Taoyuan (TW); Jhih-Shian Lee, Taoyuan (TW); Ya-Chen Chen, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 277 days.

(21) Appl. No.: 17/210,201

(22) Filed: Mar. 23, 2021

(65) Prior Publication Data
US 2021/0319599 A1    Oct. 14, 2021

Related U.S. Application Data

(60) Provisional application No. 63/009,168, filed on Apr. 13, 2020.

(51) Int. Cl.
*G06K 9/00* (2022.01)
*A61B 5/02* (2006.01)
(Continued)

(52) U.S. Cl.
CPC .............. *G06T 11/005* (2013.01); *A61B 6/03* (2013.01); *A61B 6/5217* (2013.01);
(Continued)

(58) Field of Classification Search
CPC .................................. G06K 9/00; A61B 5/02
(Continued)

(56) References Cited

U.S. PATENT DOCUMENTS 7,477,771 B2    1/2009  Iatrou et al.
10,937,209 B2*  3/2021  Lee .............. G06T 11/008
(Continued)

FOREIGN PATENT DOCUMENTS

CN    101926676 A    12/2010
CN    104382613 A    3/2015
(Continued)

OTHER PUBLICATIONS

Soenke H. Bartling, et al., "Intrinsic respiratory gating in small-animal CT", Eur Radiol (2008) 18: 1375-1384.
(Continued)

*Primary Examiner* — Seyed H Azarian
(74) *Attorney, Agent, or Firm* — Kirton McConkie; Evan R. Witt (57) ABSTRACT

A method for gating in tomographic imaging system includes steps of: (a) performing a tomographic imaging on an object with a target moving periodically along a first axis for acquiring projection images; (b) obtaining projected curves by summing up pixel values along a direction of a second axis perpendicular to the first axis in each projection image; (c) determining a target zone on the projection images, wherein a central position on the first axis of the target zone is corresponding to a position having the largest variation in the projected curves on the first axis; (d) calculating parameter values of pixel values in the target zones and obtaining a curve of a moving cycle of the target according to the parameter values; and (e) selecting the projection images under the same state in the moving cycle for image reconstruction according to the curve of the moving cycle of the target.

7 Claims, 6 Drawing Sheets

(51) Int. Cl.

| | | |
|---|---|---|
| *G06T 11/00* | (2006.01) | |
| *G06T 7/70* | (2017.01) | |
| *A61B 6/03* | (2006.01) | |
| *A61B 6/00* | (2006.01) | |
| *G01N 23/04* | (2018.01) | |
| *G06T 7/00* | (2017.01) | |

(52) U.S. Cl.
CPC .......... *A61B 6/5288* (2013.01); *G01N 23/04* (2013.01); *G06T 7/0012* (2013.01); *G06T 7/70* (2017.01); *G06T 2207/10072* (2013.01); *G06T 2207/30004* (2013.01); *G06T 2207/30168* (2013.01)

(58) Field of Classification Search
USPC ....... 382/100, 103, 107, 128–132, 168, 181, 382/199, 224, 254, 274, 286–291, 305, 382/320, 194; 600/301, 407, 481
See application file for complete search history.

(56) References Cited

U.S. PATENT DOCUMENTS

| | | | |
|---|---|---|---|
| 2004/0258286 A1* | 12/2004 | Salla | G06T 7/0016 382/128 |
| 2006/0120586 A1 | 6/2006 | Iatrou et al. | |
| 2008/0253636 A1* | 10/2008 | Deller | A61B 5/113 382/131 |
| 2017/0055920 A1 | 3/2017 | Mestha et al. | |
| 2017/0156690 A1* | 6/2017 | Yi | A61B 6/5264 |
| 2018/0182135 A1* | 6/2018 | Lee | G06T 7/285 |
| 2018/0303377 A1* | 10/2018 | West | G06F 3/011 |

FOREIGN PATENT DOCUMENTS

| | | |
|---|---|---|
| CN | 103608845 B | 10/2016 |
| CN | 108324303 A | 7/2018 |
| CN | 105069785 B | 11/2018 |
| CN | 110547822 A | 12/2019 |
| CN | 108364290 B | 10/2020 |
| WO | 2008156764 A1 | 12/2008 |
| WO | 2010025946 A1 | 3/2010 |
| WO | 2015126189 A1 | 8/2015 |

OTHER PUBLICATIONS

J Kuntz, et al., "Fully automated intrinsic respiratory and cardiac gating for small animal CT", Phys. Med. Biol. 55 (2010) 2069-2085.

Xuan Liu, et al., "A comparison study: image-based vs signal-based retrospective gating on micro-CT", Conference: Developments in X-Ray Tomography XI, Sep. 2017.

S.M. Johnston et al., Phase-selective image reconstruction of the lungs in small animals using Micro-CT, Physics of Medical Imaging, Proc. of SPIE vol. 7622, 2010.

Seonyeong Park et al., A Novel Method of Cone Beam CT Projection Binning based on Image Registration, IEEE Trans Med Imaging, Aug. 2017, pp. 1733-7145.

Haraold Seigarth, MD et al., Electrocardiogram-Independent Image Reconstruction in Cardiac Multidetector Computed Tomography Using Retrospective Motion Synchronization, Investigative Radiology, vol. 41, No. 12, Dec. 2006, pp. 898-903.

Geoffrey D. Hugo et al., Advances in 4D radiation therapy for managing respiration: Part I—4D imaging, Z. Med. Phys., 2012, pp. 258-271.

Rachael Martin et al., Evaluation of intrinsic respiratory signal determination methods for 4D CBCT adapted for mice, American Association of Physicists in Medicine, 2015.

\* cited by examiner

METHOD FOR GATING IN TOMOGRAPHIC IMAGING SYSTEM

CROSS-REFERENCE TO RELATED APPLICATION

This application claims the benefit of U.S. Provisional Application No. 63/009,168 filed on Apr. 13, 2020, entitled "Method for Image-based Gating in Tomographic Imaging System". The entire contents of the above-mentioned patent application are incorporated herein by reference for all purposes.

FIELD OF THE INVENTION

The present disclosure relates to a method for gating in tomographic imaging system, and more particularly to a method for image-based gating in tomographic imaging system.

BACKGROUND OF THE INVENTION

Tomographic imaging system includes computed tomography (CT), positron emission tomography (PET), and single photon emission computed tomography (SPECT), etc. When the CT scan is performed, the light source (e.g. X-ray) and the detector are regularly moved around the detected object to emit x-ray and acquire image data by 180 (or more, or less) degrees, so as to collect the projection images at different angles. Based on the projection images, an image reconstruction is performed by the computer, and the cross-sectional tomographic image of the detected object is formed. Further, the three-dimensional image of the detected object is formed by the multiple tomographic images.

If the detected object is a living body, the organs (e.g. lung, heart) of the detected object may move periodically due to breath or heartbeat. Therefore, the organs of the detected object in the projection images at different angles are not static. Accordingly, the formed tomographic image would be blurred due to the movement of the organs.

The gating technique is developed for obviating blurred images caused by the periodical movement of the organs. Conventionally, the gating technique is a prospective gating technique, which is illustrated as follows.

Figure 1:
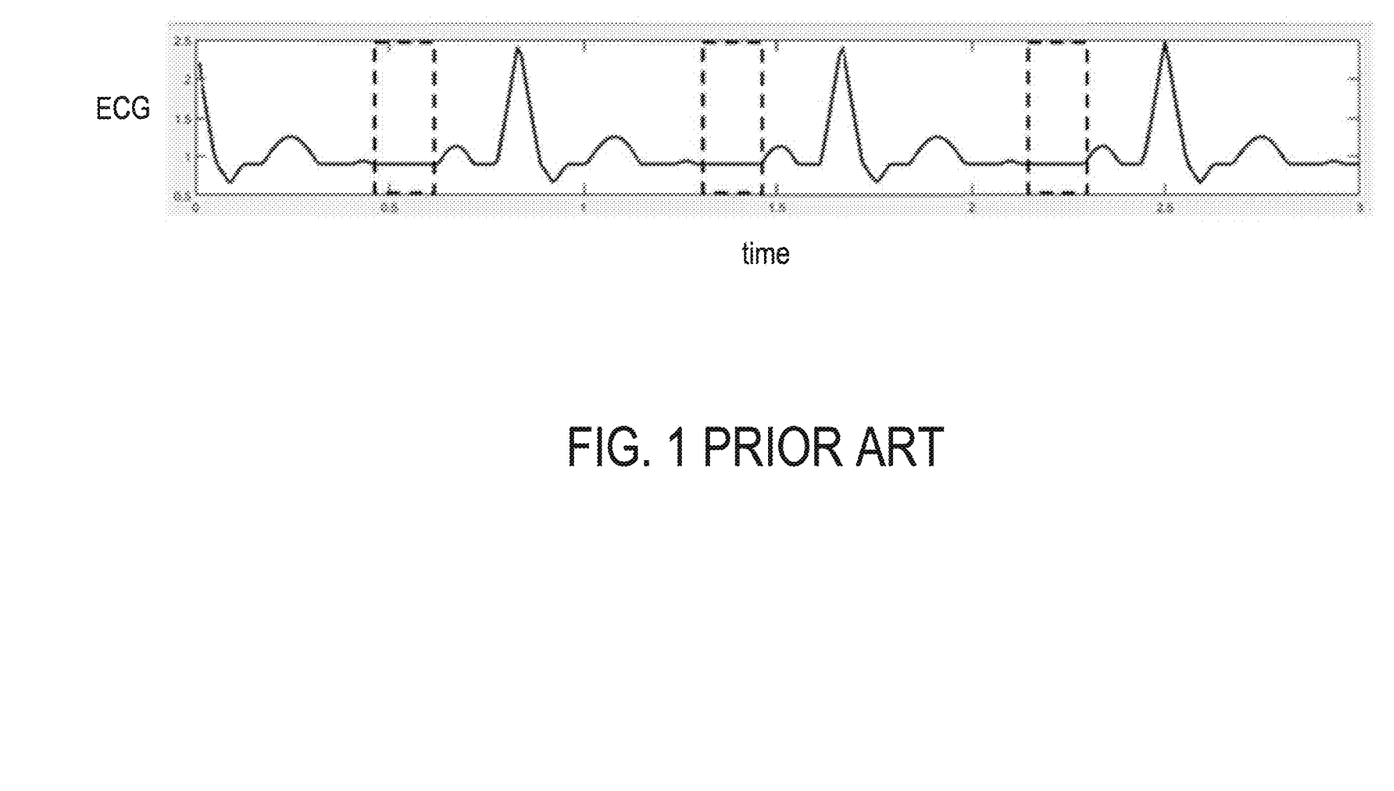
FIG. 1 schematically shows the timing of performing tomographic imaging in the conventional prospective gating method.

In the prospective gating technique, the tomographic imaging system has to be connected with the external physiological monitoring apparatus, e.g., Electrocardiography (ECG) machine, piezoelectric sensor. The tomographic imaging system synchronizes with the physiological signal to acquire projection images in a specific state of period. An example of prospective gating for tomographic imaging is shown in FIG. 1. It is noted that the projection images are acquired only during the period marked by dashed blocks. Accordingly, the acquired multi-angle projection images under the same physiological period are utilized for image reconstruction. Consequently, the tomographic images under the specific physiological state are obtained, and blurred images caused by movement on the tomographic images can be reduced. However, the disadvantage of this prospective gating technique is that the tomographic imaging system has to be connected with the external physiological monitoring apparatus, which increases the cost a lot. In addition, it is also a technical challenge to synchronize the tomographic imaging system and the physiological monitoring apparatus.

Therefore, there is a need of providing a method for gating in tomographic imaging system to obviate the drawbacks encountered from the prior arts.

SUMMARY OF THE INVENTION

It is an objective of the present disclosure to provide a method for gating in tomographic imaging system. When the tomographic imaging is performed, the projection images are acquired continuously. After the projection images are all collected, the projection images are processed according to the characteristics thereof. Particularly, the projection images under the same physiological state are selected. Accordingly, in the method for gating in tomographic imaging system of the present disclosure, there is no need to connect the tomographic imaging system with any external physiological monitoring apparatus.

In accordance with an aspect of the present disclosure, there is provided a method for gating in tomographic imaging system. The method includes steps of: (a) performing a tomographic imaging on an object for acquiring a plurality of projection images at different angles, wherein a target of the object in the projection images moves periodically along a first axis; (b) obtaining a plurality of projected curves by summing up pixel values along a direction of a second axis, which is perpendicular to the first axis, in each of the projection images; (c) determining a target zone on the projection images, wherein the target is located in the target zone, and a central position on the first axis of the target zone is corresponding to a position having the largest variation in the projected curves on the first axis; (d) calculating parameter values of pixel values in the target zone on the projection images, and obtaining a curve of a moving cycle of the target according to the parameter values; and (e) selecting the projection images under the same state in the moving cycle for image reconstruction according to the curve of the moving cycle of the target.

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 2:
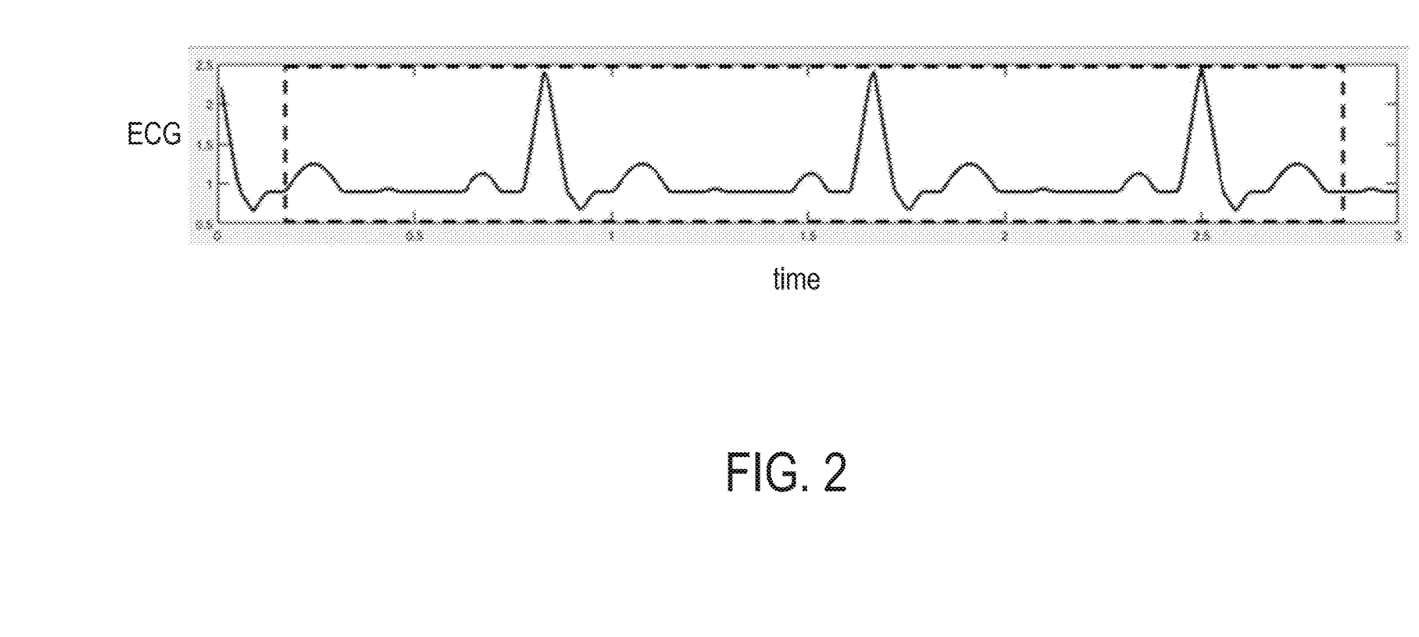
FIG. 2 schematically shows the timing of performing tomographic imaging in a method for gating of the present disclosure.

The method for gating in tomographic imaging system of the present disclosure utilizes a retrospective gating technique. When the tomographic imaging is performed, as shown in FIG. 2, the projection images are acquired continuously during the period marked by dashed block. Particularly, the present disclosure utilizes the retrospective gated tomographic imaging system for gating to obviate blurred images caused by the periodical movement of the organs due to breath or heartbeat.

Figure 3:
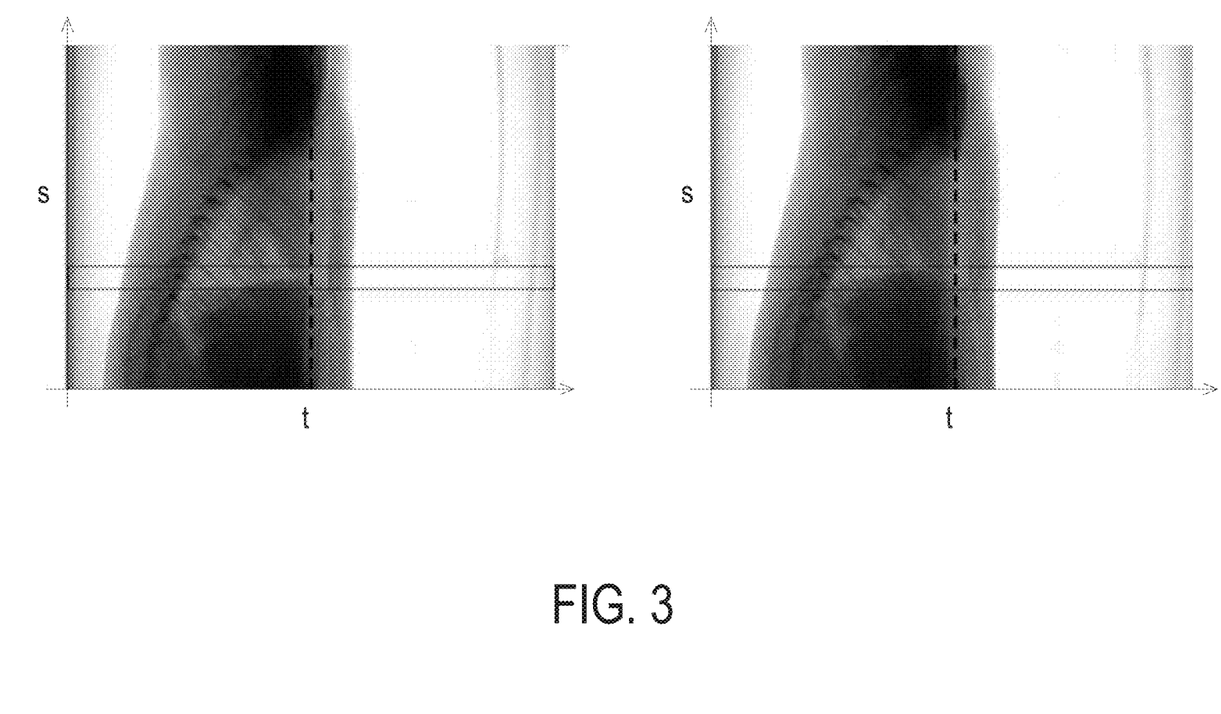
FIG. 3 schematically shows the projection images taken at different angles.

When the tomographic imaging is performed, the light source, e.g., X-ray, and the detector are regularly moved around the detected object, so as to collect the projection images at different angles. If the detected object is a living body, the organs of the detected object may move periodically due to breath or heartbeat. Therefore, the projection images at different angles are not static. For example, the detected object is a mouse, and FIG. 3 shows the projection images of a mouse taken at different angles. The light source and the detector are rotated relative to the rotation axis which is depicted by the dashed line. The diaphragm of the mouse is located in the zone marked by the solid-line block, whose position is predetermined manually and needs to be further corrected. It is observed that the diaphragm moves upwardly or downwardly in different projection images due to breath.

In order to figure out the respiratory state to which every projection image is corresponding, the position of the organ or zone affected by breathing on the projection image should be detected. Taking the diaphragm as an example of a target that moves periodically in the detected object, the way of computing the position of the diaphragm is described as follows.

Figure 4:
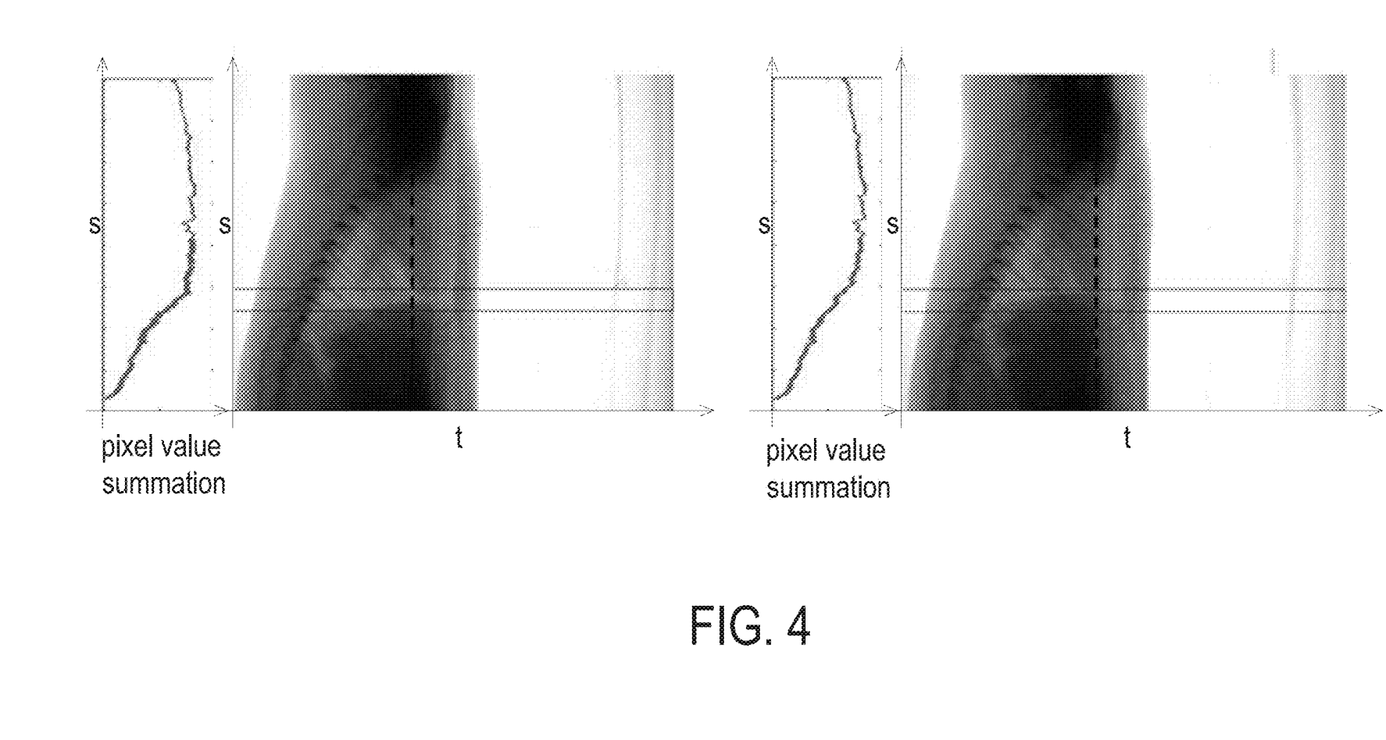
FIG. 4 schematically shows the projection images taken at different angles and the corresponding projected curves.

The light source and the detector rotate around the rotation axis to perform the tomographic imaging for the detected object. When the tomographic imaging is performed, the projection images at different angles are acquired continuously. The number of the projection images is N, being a positive integer, which can be determined according to the required image quality of the tomographic image formed based on the projection images. For example, the larger N is, the better the signal to noise ratio of the tomographic image is (i.e., the better the image quality of the tomographic image is). FIG. 4 schematically shows two projection images at two different angles. As shown in FIG. 4, the rotation axis is parallel to a first axis s, the diaphragm in the projection images moves upwardly or downwardly along the first axis s, and a second axis t is perpendicular to the first axis s.

According to equation (1), in N projection images $P_{\theta ts}$ of different angles θ, N projected curves $C_{\theta ts}$ are obtained by summing up the pixel values along the direction of the second axis t in every projection image. In all the angles θ that the N projection images are taken at respectively, the difference between the first angle and the final angle is preferably but not limited to be larger than 180 degrees. Moreover, in equation (1), T is the number of the pixels in the direction of the second axis t in the projection image.

$$C_{\theta ts} = \sum_{t=1}^{T} P_{\theta ts} \quad (1)$$

Taking FIG. 4 as an example, the projected curve is shown beside the corresponding projection image. The projected curve is a curve of the sum of the pixel values of each of the projection images versus the position along the first axis s. In particular, each point on the projected curve is corresponding to a pixel value summation and a position on the first axis s, where the said pixel value summation is the sum of the pixel values of all the pixels along the direction of the second axis t corresponding to the said position. That is, each of the projection images is projected along the first axis s to obtain the corresponding projected curve.

Then a diaphragm zone (target zone) where the diaphragm is located on the projection images is further determined. The diaphragm zone has a central position on the first axis corresponding to a position having the largest variation in the projected curves on the first axis s. For example, the projection image is regarded as a matrix of pixel values with a plurality of rows along the first axis s. The pixel values on each row are summed up to obtain the projected curve, and the row having the largest variation of the pixel value summation is the central position of the diaphragm zone. In an embodiment, in the N projected curves $C_{\theta ts}$, the coefficients of variation or the standard deviations along the time sequence are calculated, and the position on the first axis s having the largest coefficient of variation or the largest standard deviation is the central position on the first axis s of the diaphragm zone. As shown in FIG. 4, the diaphragm zone in the projection image is marked automatically by a block, which is the solid-line block parallel to the second axis t. In specific, the dimension of the solid-line block is predetermined based on a general diaphragm size but not limited thereto. Once the central position of the diaphragm zone is determined, the diaphragm zone can be automatically marked by the block.

Since the detected object is always in the range of imaging during rotation, to sum up the pixel values along the second axis t can avoid the deviation caused by rotation. Therefore, the respiration curve obtained in the succeeding steps can be more accurate.

After the diaphragm zone is determined, the parameter value (e.g., maximum, minimum, average, median, summation or quartile) of the pixel values in the diaphragm zone on the projection image is calculated. Then the curve of the moving cycle of the diaphragm, i.e. the respiration curve, is obtained according to the parameter values. For example, the curve of the moving cycle of the diaphragm is a graph of the parameter value versus time, or a graph of the parameter value versus a serial number of the projection images.

Figure 5:
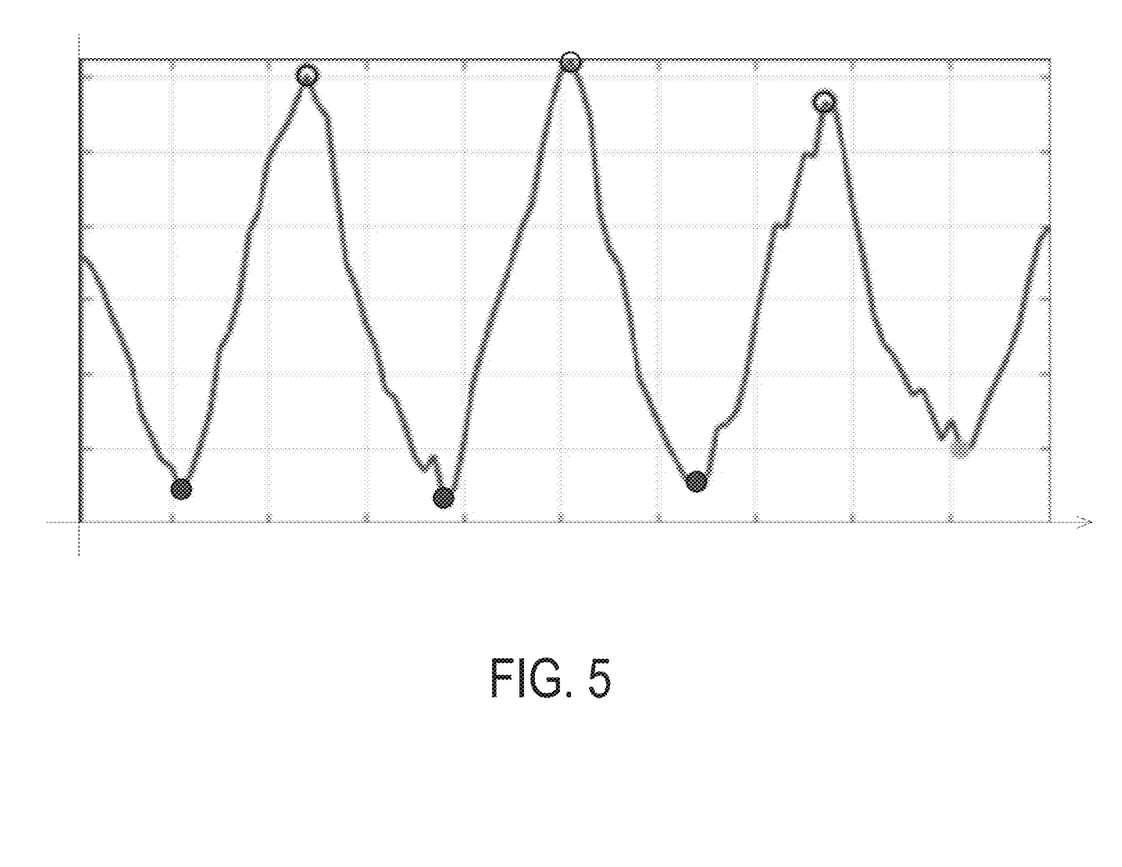
FIG. 5 schematically shows the respiration curve obtained by the method for gating of the present disclosure.

As shown in FIG. 5, the respiration curve can be obtained according to the parameter values of the N projection images taken at different angles. The projection images under the same state in the respiratory cycle (i.e., the projection images taken at the same timing in the respiratory cycle) are selected for image reconstruction, and the definition of the diaphragm tomographic image is improved. For example, the projection images at the timing marked by the hollow circles are selected for image reconstruction, or the projection images at the timing marked by the solid circles are selected for image reconstruction. In FIG. 5, the transverse axis represents the time or the serial number of the projection images, and the vertical axis represents the parameter value of the pixel values.

Figure 6:
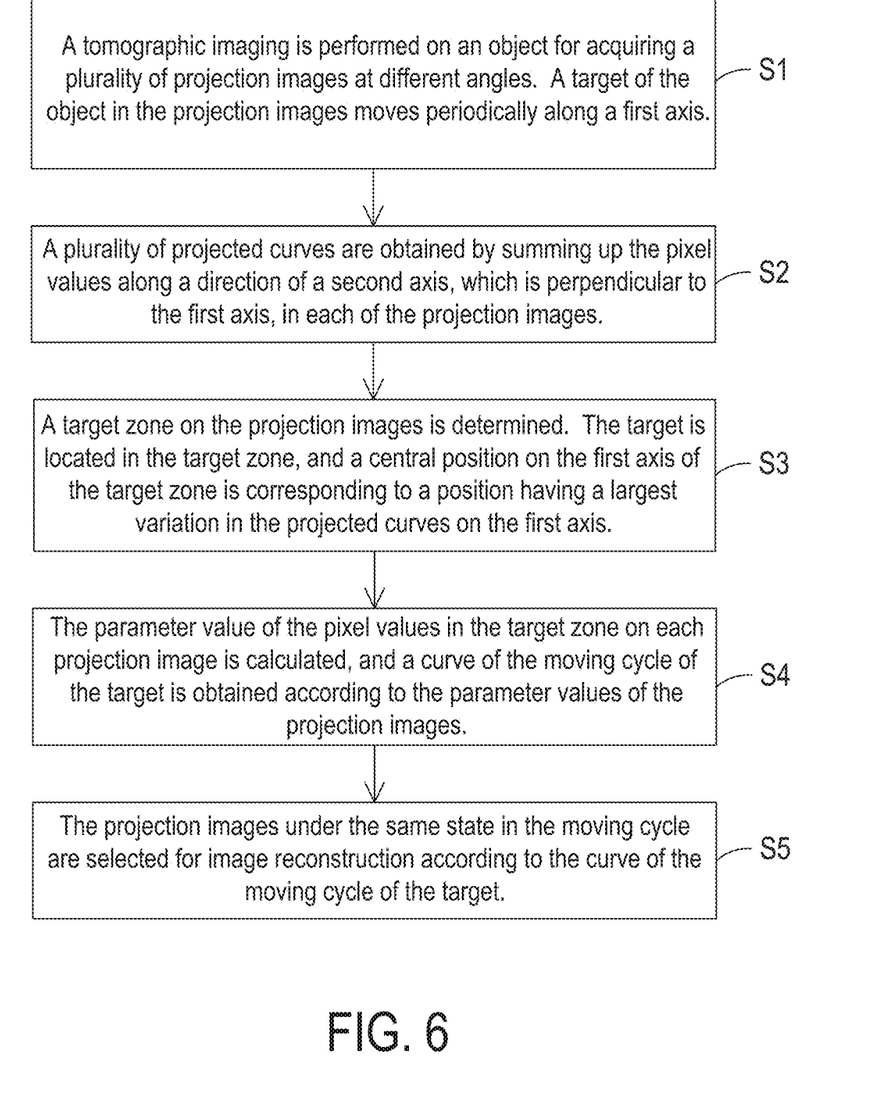
FIG. 6 is a schematic flow chart illustrating a method for gating in tomographic imaging system according to an embodiment of the present disclosure.

FIG. 6 is a schematic flow chart illustrating a method for gating in tomographic imaging system according to an embodiment of the present disclosure. Based on the above illustration, the method for gating in tomographic imaging system of the present disclosure can be generalized to include the steps shown in FIG. 6.

First, in step S1, a tomographic imaging is performed on an object for acquiring a plurality of projection images at different angles. A target of the object in the projection images moves periodically along a first axis, which is parallel to a rotation axis of the light source and the detector.

Then, in step S2, a plurality of projected curves are obtained by summing up the pixel values along the direction of a second axis, which is perpendicular to the first axis, in each of the projection images.

Then, in step S3, a target zone on the projection images is determined. The target is located in the target zone, and a central position on the first axis of the target zone is corresponding to a position having the largest variation in the projected curves on the first axis. In an embodiment, in the projected curves, the coefficients of variation or the standard deviations along the time sequence are calculated, and the position having the largest coefficient of variation or the largest standard deviation is the central position of the target zone.

Afterward, in step S4, the parameter value of the pixel values in the target zone on each projection image is calculated, and a curve of the moving cycle of the target is obtained according to the parameter values of the projection images.

Finally, in step S5, the projection images under the same state in the moving cycle are selected for image reconstruction according to the curve of the moving cycle of the target.

In the embodiments shown in FIGS. 2-5, the detected object is a living body, and the target is the diaphragm, which moves periodically due to breath. Through the steps shown in FIG. 6, the projection images under the same state in the respiratory cycle are picked out for image reconstruction. Meanwhile, there is no need to connect the tomographic imaging system with any external physiological monitoring apparatus.

In another embodiment, the target may also be the heart, which moves periodically due to heartbeat, and the similar technique can also be applied to heart gating.

From the above descriptions, the present disclosure provides a method for gating in tomographic imaging system. When the tomographic imaging is performed, the projection images are acquired continuously. After the projection images are all collected, the projection images are processed according to the characteristics thereof. Particularly, the projection images under the same physiological state are picked out. Accordingly, in the method for gating in tomographic imaging system of the present disclosure, there is no need to connect the tomographic imaging system with any external physiological monitoring apparatus.

While the disclosure has been described in terms of what is presently considered to be the most practical and preferred embodiments, it is to be understood that the disclosure needs not be limited to the disclosed embodiment.

What is claimed is:

1. A method for gating in tomographic imaging system, comprising: (a) performing a tomographic imaging on an object for acquiring a plurality of projection images at different angles, wherein a target of the object in the projection images moves periodically along a first axis; (b) obtaining a plurality of projected curves by summing up pixel values along a direction of a second axis, which is perpendicular to the first axis, in each of the projection images; (c) determining a target zone on the projection images, wherein the target is located in the target zone, and a central position on the first axis of the target zone is corresponding to a position having a largest variation in the projected curves on the first axis; (d) calculating a parameter value of the pixel values in the target zone on each of the projection images, and obtaining a curve of a moving cycle of the target according to the parameter values of the projection images; and (e) selecting the projection images under the same state in the moving cycle for image reconstruction according to the curve of the moving cycle of the target;

wherein each of the projection images is regarded as a matrix of pixel values with a plurality of rows along the first axis, the pixel values on each row are summed up, and the row having the largest variation of the sum of the pixel values in the projection images is the central position of the target zone;

wherein in the projected curves, coefficients of variation or standard deviations along a time sequence are calculated, and a position on the first axis having a largest coefficient of variation or the largest standard deviation corresponds to the central position on the first axis of the target zone.

2. The method according to claim 1, wherein the projected curve is obtained according to following equation:

$$C_{\theta ts} = \sum_{t=1}^{T} P_{\theta ts},$$

where $C_{\theta ts}$ is the projected curve, T is a number of pixels in the direction of the second axis in the projection image, and $P_{\theta ts}$ is the projection image.

3. The method according to claim 1, wherein when the tomographic imaging is performed, a light source and a detector are regularly moved around the object for acquiring the projection images at the different angles.

4. The method according to claim 3, wherein the light source and the detector are rotated relative to a rotation axis parallel to the first axis.

5. The method according to claim 1, wherein a number of the projection images is determined according to a required image quality of a tomographic image formed based on the projection images.

6. The method according to claim 1, wherein the parameter value is a maximum, a minimum, an average, a median, a summation or a quartile of the pixel values in the target zone.

7. The method according to claim 1, wherein the curve of the moving cycle of the target is a graph of the parameter value versus time, or a graph of the parameter value versus a serial number of the projection images.

* * * * *